(12) United States Patent
Kusaki et al.

(10) Patent No.: US 9,410,951 B2
(45) Date of Patent: Aug. 9, 2016

(54) METHOD FOR PRODUCING SUBSTRATE FOR MAKING MICROARRAY

(75) Inventors: Wataru Kusaki, Jyoetsu (JP); Takeshi Kinsho, Jyoetsu (JP); Toshinobu Ishihara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1341 days.

(21) Appl. No.: 12/458,637

(22) Filed: Jul. 17, 2009

(65) Prior Publication Data

US 2010/0055337 A1    Mar. 4, 2010

(30) Foreign Application Priority Data

Sep. 1, 2008   (JP) .................................. 2008-223026

(51) Int. Cl.
| | | |
|---|---|---|
| G01N 33/543 | (2006.01) | |
| C40B 40/04 | (2006.01) | |
| C40B 50/18 | (2006.01) | |

(52) U.S. Cl.
CPC .......... *G01N 33/54353* (2013.01); *C40B 40/04* (2013.01); *C40B 50/18* (2013.01); *B01J 2219/00527* (2013.01); *B01J 2219/00596* (2013.01); *B01J 2219/00612* (2013.01); *B01J 2219/00626* (2013.01); *B01J 2219/00637* (2013.01); *B01J 2219/00659* (2013.01)

(58) Field of Classification Search
CPC ... C04B 40/04; C04B 50/18; G01N 33/54353
USPC ......... 427/2.11, 2.12, 2.13, 409, 410; 435/7.1
See application file for complete search history.

(56) References Cited

U.S. PATENT DOCUMENTS

2006/0234308 A1\* 10/2006 Schneider-Mergener et al. .............................. 435/7.1
2008/0292863 A1\* 11/2008 Yagihashi et al. ......... 428/304.4

FOREIGN PATENT DOCUMENTS

| JP | A-63-211300 | 9/1988 |
| JP | A-04-182491 | 6/1992 |
| JP | A-04-221630 | 8/1992 |
| JP | A-2007-518075 | 7/2007 |
| WO | WO 2005/066612 A2 | 7/2005 |

OTHER PUBLICATIONS

Japanese Office Action issued in Japanese Patent Application No. 2008-223026 dated Nov. 24, 2010 (with translation).
Sugimura et al., Microfabrication Based on Self-assembled Monolayer Resists and Wet-chemical Processes, Journal of the Surface Science Society of Japan, vol. 22, No. 6, pp. 364-369, 2001, with Abstract.

\* cited by examiner

*Primary Examiner* — Mathieu Vargot
(74) *Attorney, Agent, or Firm* — Oliff PLC

(57) ABSTRACT

There is disclosed a method for producing a substrate for making a microarray, the method comprising: at least, a step of forming a monomolecular film having orientated oxysilanyl groups toward an outmost surface on the substrate; and a step of forming a monomolecular film having orientated amino groups toward an outmost surface on the substrate by applying a solution containing a diamine compound to the oxysilanyl groups. There can be provided a method for producing a substrate for making a microarray in which density and orientation of amino groups orientated toward an outmost surface are controllable, and in addition, there is no delamination of a monomolecular film formed on the substrate.

5 Claims, 1 Drawing Sheet

(1)

(2)

(3)

(4)

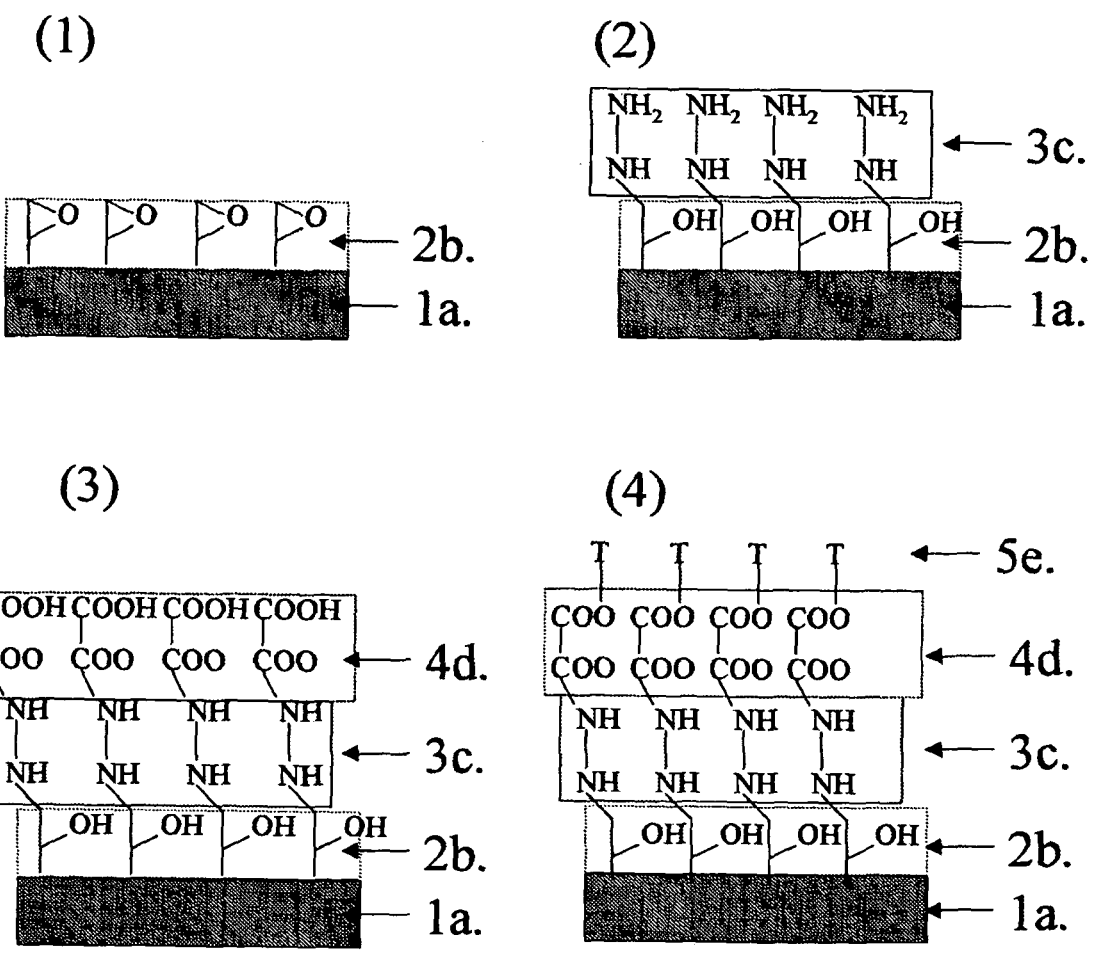

METHOD FOR PRODUCING SUBSTRATE FOR MAKING MICROARRAY

BACKGROUND OF THE INVENTION

1. Field of the Invention

The present invention relates to a testing technique using a biomolecule, in particular a testing technique on a gene sequence such as a DNA sequencing analysis and a genetic diagnosis, and a testing technique on decomposition of a substrate by using an immobilized protein (enzyme), and a method for producing a substrate for making an analysis device used in the analysis of those as mentioned above.

2. Description of the Related Art

An analysis of a DNA sequence of genes including a human genome analysis has been rapidly progressing in recent years, and based on those information, it is advancing to a research on a gene function, a diagnosis on a disease caused by a gene, and so on. Furthermore, as a technique to perform analysis of these genes and research on a gene function in a large scale and in a short time, a number of researches on so-called a DNA chip and a DNA microarray are being made.

A DNA microarray is to detect a DNA strand having its complementary sequence in a sample by immobilizing a DNA with a specific sequence in a very narrow space. As a method for DNA immobilization, a stamping method using a pin, a bubble jet method (registered trade mark), and a method using a photolithography technique are known.

A substrate used for immobilizing these biomolecules is generally formed by introducing an amino group on its surface by applying mainly polylysine and an aminosilane on the substrate because a nucleic acid, an amino acid, and a protein may be immobilized on a substrate having an amino group.

However, in the method to apply polylysine and an aminosilane on a substrate as mentioned above, controls of a film thickness of polylysine and the aminosilane, and of a density and an orientation of the amino group are difficult, so that, in immobilization of a biomolecule, there are problems of causing a variation among substrates and a variation in amount of the immobilized biomolecule among immobilization spots. Depending on a processing method, these films may be delaminated in a certain case. These variations eventually lead to a fluctuation in detection results, which is a big problem in determining whether detected or not detected.

Accordingly, in order to improve a detection sensitivity of biomolecules such as a nucleic acid, an amino acid, and a protein, and also to establish a detection method of them, a method for producing a substrate for making a microarray having orientated amino groups toward an outmost surface in a controllable way to give uniform immobilization of a biomolecule on the entire surface without variation among substrates and variation in an immobilized amount among immobilization spots has been desired.

SUMMARY OF THE INVENTION

The present invention was made in view of the above situation, and has an object to provide a method for producing a substrate for making an undelaminating microarray controllable in density and orientation of amino groups, wherein the method comprises: a step of forming a monomolecular film having orientated oxysilanyl groups toward an outmost surface on the substrate; and a step of forming a monomolecular film having orientated amino groups toward an outmost surface on the substrate by applying a solution containing a diamine compound to the oxysilanyl groups.

In order to solve the problems as mentioned above, the present invention provides a method for producing a substrate for making a microarray, the method comprising: at least, a step of forming a monomolecular film having orientated oxysilanyl groups toward an outmost surface on a substrate; and a step of forming a monomolecular film having orientated amino groups toward an outmost surface on the substrate by applying a solution containing a diamine compound to the oxysilanyl groups.

Consequently, because density and orientation of amino groups may be controllable by forming a monomolecular film having orientated amino groups toward an outmost surface on a substrate by applying a solution containing a diamine compound to a monomolecular film having orientated oxysilanyl groups toward an outmost surface, a biomolecule may be immobilized under a uniform condition in an entire film surface in a step following thereafter. A substrate produced by the present method has a sufficient delamination resistance.

The afore-mentioned diamine compound may be a diamine compound represented by the following general formula (1):

$$NH_2\text{-}Z\text{-}NH_2 \qquad (1)$$

wherein, Z represents a linear, a branched, or a cyclic divalent alkylene group having 1 to 20 carbon atoms with a hydrogen atom in the group being optionally substituted by a halogen atom, a hydroxyl group, and a cyano group, and a methylene group in the group being optionally substituted by an oxygen atom (—O—) or a carbonyloxy group (—O—CO—) and optionally containing a double bond (C=C) or a triple bond (C≡C).

Accordingly, below-mentioned compounds may be cited as specific examples of the diamine compound.

Here, a structure represented by Z between two amino groups in the general formula (1) contains preferably an alkylene group having 8 to 16 chain carbon atoms (and optionally containing one or more double bonds in the carbon chain) in case of the structure being linear or branched, and an aryl group in case of the structure being cyclic.

Consequently, by using a diamine compound containing an alkylene group having 8 to 16 chain carbon atoms in case of the structure between two amino groups in the diamine compound being linear or branched, or a diamine compound containing an aryl group in case of the structure being cyclic, a monomolecular film may be formed by an intermolecular interaction, namely by a self-assembly. With this, a monomolecular film having orientated amino groups toward an outmost surface may be formed stably, thereby enabling to form a substrate for making a microarray with high resistances to delamination and to the subsequent processing operations of the substrate.

In addition, an amine compound having the same Z as the diamine compound in the general formula (1) with one of the two amino groups bonded to Z being a methyl group may be further contained in the solution containing the diamine compound.

With this, a surface wetting property may be manipulated, and thus it is significant in its production in a certain case.

Further, the step of forming the monomolecular film having orientated oxysilane groups toward an outmost surface on the substrate may be performed by soaking the substrate into a solution containing a silane compound having an oxysilanyl group.

Consequently, when a silane compound containing an oxysilanyl group is used in the step of forming a monomolecular film having orientated oxysilanyl groups toward an outmost surface on the substrate, a monomolecular film may be formed cheaply and more easily.

Further, the silane compound containing the oxysilanyl group is preferably a silane compound represented by the following general formula (2):

$$Y_3Si-(CH_2)_m-X \quad (2)$$

wherein, a reference character "m" represents an integer of 3 to 16; X represents an oxysilanyl group; and Y independently represents a halogen atom or an alkoxy group having 1 to 4 carbon atoms.

Consequently, by using a silane compound represented by the general formula (2), a monomolecular film may be formed by a self-assembly of molecules to be immobilized, which is preferable because a fine and oriented monomolecular film may be formed.

In the step of forming the monomolecular film having the orientated oxysilanyl groups toward an outmost surface on the substrate by using the silane compound having the oxysilanyl group represented by the general formula (2), the monomolecular film may be formed by using a mixture prepared by mixing the silane compound with at least one kind of silane compounds represented by the following general formulae (3) and (4):

$$Y'_3Si-(CH_2)_n-CH_3 \quad (3)$$

$$Y'_3Si-(CH_2)_n-OCH_3 \quad (4)$$

wherein, a reference character "n" represents an integer of 0 to a reference character "m": the reference character "m" represents the value in the general formula (2); and Y' represents a halogen atom or an alkoxy group having 1 to 4 carbon atoms.

Consequently, when the monomolecular film is formed by using the mixture prepared by mixing at least one kind of the silane compounds represented by the above general formulae (3) and (4), a reaction among nearby oxysilanyl groups accompanying a ring-opening of the oxysilanyl group to inhibit a reaction with an amino group may be avoided.

In the step of forming the monomolecular film having the orientated oxysilanyl groups toward an outmost surface on the substrate by using the silane compound having the oxysilanyl group represented by the general formula (2), a catalyst to be mixed along with the silane compound may be a nitrogen-containing organic base.

As shown above, when a nitrogen-containing organic base is mixed, as the catalyst, with the silane compound, the monomolecular film may be formed more easily, which is preferable consequently.

In this case, the nitrogen-containing organic base may be a pyrrolidine derivative or a piperidine derivative.

As shown above, when a pyrrolidine derivative or a piperidine derivative is used as the nitrogen-containing base, the monomolecular film may be formed further more easily, which is preferable consequently.

In addition, a concentration ratio of the silane compound and the nitrogen-containing organic base may be made such that a mol ratio of the nitrogen-containing organic base is 0.1 to 100 by mol relative to 1 mol of the silane compound.

As shown above, when a concentration ratio of the silane compound and the nitrogen-containing organic base is made such that a mol ratio of the nitrogen-containing organic base is 0.1 to 100 by mol relative to 1 mol of the silane compound, the monomolecular film may be formed further more easily, which is preferable consequently.

In addition, the microarray may be used for a testing of a biomolecule.

Consequently, the microarray may be used for a testing relating to a biomolecule.

In addition, the biomolecule may be a nucleic acid or a protein.

Consequently, the microarray may be used for a testing relating to a biomolecule, in particular a nucleic acid or a protein.

As explained above, when a method of the present invention for producing a substrate for making a microarray is used, a substrate for making a microarray having orientated amino groups toward an outmost surface may be formed, and thus the subsequent immobilization of a biomaterial may be done under a uniform condition in an entire surface. In addition, because a monomolecular film produced by the present method has a sufficient delamination resistance in subsequent processing operations of the substrate, a substrate for making a microarray of more finely processable with a high precision may be obtained easily and conveniently.

BRIEF DESCRIPTION OF THE DRAWING

FIG. 1 is a schematic diagram showing an example of the method for producing a substrate for making a microarray in the present invention.

DETAILED DESCRIPTION OF THE PREFERRED EMBODIMENTS

Hereinafter, the present invention will be explained more specifically.

As mentioned above, in the past a substrate used for immobilizing biomolecules has been generally formed by introducing amino groups on its surface by applying mainly polylysine and an aminosilane on a substrate because a nucleic acid, an amino acid, and a protein may be immobilized on a substrate having an amino group. However, controls of a film thickness of polylysine and the aminosilane, and of a density and an orientation of the amino groups are difficult, so that, in immobilization of a biomolecule, there are problems of causing a variation among substrates and a variation in amounts of the immobilized biomolecule among immobilization spots. Depending on a processing method, there may be a case in which these films are delaminated. These variations eventually lead to the fluctuation in detection results, which is a big problem in determining whether detected or not detected.

Accordingly, the inventors of the present invention initiated to develop a method for producing a substrate for making a microarray having orientated amino groups toward an outmost surface, capable of immobilizing a biomolecule under an uniform condition in an entire film surface in subsequent steps, and having a sufficient delamination resistance. As a result, they found a method for producing a substrate for making a microarray having orientated amino groups toward an outmost surface thereby rendered with a film controllable as a monomolecular film by incorporating at least a step of forming a monomolecular film having orientated oxysilanyl groups toward an outmost surface on a substrate and a step of forming a monomolecular film having orientated amino groups toward an outmost surface on the substrate by applying a solution containing a diamine compound to the oxysilanyl groups. In the substrate produced by this method, a density and an orientation of the amino groups may be controllable, and thus a biomolecule may be immobilized under a uniform condition in an entire film surface in subsequent steps. In addition, because a monomolecular film produced by the present method has a sufficient delamination resistance in subsequent processes, a substrate for making a microarray of more finely processable with a high precision may be obtained.

Namely, the present invention relates to a method for producing a substrate for making a microarray, the method comprising: at least, a step of forming a monomolecular film having orientated oxysilanyl groups toward an outmost surface on a substrate; and a step of forming a monomolecular film having orientated amino groups toward an outmost surface on the substrate by applying a solution containing a diamine compound to the oxysilanyl groups.

A microarray obtained from a substrate for making a microarray produced by the present invention may be produced by using methods such as a stamping method using a pin, a bubble jet method (registered trade mark), and a method using a photolithography technique.

In the case where the outermost surface of a substrate for immobilization is a metal oxide layer when applying a method of the present invention, owing to sufficient hydroxyl groups on the surface, a monomolecular film having a silicon oxide chain may be formed by directly treating the surface by a silane compound to be described later. In the case where the outermost surface is a metal layer, a natural oxide layer in the outermost layer may be used, or a layer oxidized only near the outermost surface by using ozone, an aqueous hydrogen peroxide, water, an oxygen plasma, and the like may be used. In a non-electrical detection method, there may be assumed a case to apply on a resin substrate, and for that case Japanese Patent Application Laid-Open (kokai) No. H4-221630 teaches that a monomolecular film having a silicon oxide chain can be formed by treating the surface by an electron beam or an ion beam under an oxygen atmosphere.

A monomolecular film may be formed on an entire substrate surface, but generally it is formed only on a necessary part where a resist film is used to form the monomolecular film regioselectively. This operation is well known, and the resist to be used therein is not particularly limited, but use of a chemically-amplified resist is preferable in view of further finer regioselective treatment.

Hiroyuki Sugimura and Osamu Takai, Journal of the Surface Science Society of Japan, 22, 364 (2001) discloses, as a method for forming a monomolecular film by using a silane compound having an oxysilanyl group only on a necessary part, a method in which the silane compound may be removed by irradiating an UV beam to an unnecessary part.

In the step of forming a monomolecular film having orientated oxysilanyl groups toward an outmost surface on a substrate, a monomolecular film having orientated oxysilanyl groups toward an outmost surface is formed on the substrate by soaking (i) a substrate treated by the above-mentioned methods, namely a substrate having a formed resist pattern protecting the surface other than the place where a recognizing material is immobilized, (ii) a substrate whose unnecessary part is removed after formation of a monomolecular film by an UV irradiation after immobilization, or (iii) a non-laminated substrate not particularly having a resist pattern in the case when the entire surface may be treated, in a solution containing a silane compound, for examples, a compound represented by the following general formula (2):

wherein, a reference character "m" represents an integer of 3 to 16; X represents an oxysilanyl group; and Y independently represents a halogen atom or an alkoxy group having 1 to 4 carbon atoms.

In the above general formula, when the reference character "m" is 3 or more, a monomolecular film may be formed. However, as will be mentioned later, when a method to form a space for an immobilized material is applied, the reference character "m" is preferably 5 or more, and more preferably 8 or more.

At the time of forming a monomolecular film having orientated amino groups toward an outmost surface on a substrate by applying a solution containing a diamine compound, there may be assumed a case where a reaction among nearby oxysilanyl groups accompanying a ring-opening of the oxysilanyl group occurs thereby inhibiting a reaction with an amino group in the diamine compound. In order to avoid it, too, it is preferable to use a mixture containing, in addition to a silane compound represented by the above general formula (2), at least one kind of a silane compound having an alkyl chain with a comparatively short total chain represented by the following general formulae (3) and (4):

wherein, a reference character "n" represents an integer of 0 to "m"; a reference character "m" represents the value in the general formula (2); and Y' represents a halogen atom or an alkoxy group having 1 to 4 carbon atoms. Further, the amount of a compound represented by the general formula (3) or (4) to be used is preferably 1 or more by equivalent mol and more preferably 4 or more by equivalent mol relative to a silane compound represented by the general formula (2). In order to secure an immobilized amount, the amount of a compound is preferably 50 or less by equivalent mol and more preferably 20 or less by equivalent mol.

In the step of forming a monomolecular film having orientated oxysilanyl groups on a substrate in the present invention, examples of the nitrogen-containing organic base to be mixed as the catalyst along with a silane compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, amides, imides, and carbamates.

Specific examples of aliphatic amines include primary aliphatic amines such as ammonia, methyl amine, ethyl amine, n-propyl amine, isopropyl amine, n-butyl amine, isobutyl amine, sec-butyl amine, tert-butyl amine, pentyl amine, tert-amyl amine, cyclopentyl amine, hexyl amine, cyclohexyl amine, heptyl amine, octyl amine, nonyl amine, decyl amine, dodecyl amine, cetyl amine, methylene diamine, ethylene diamine, and tetraethylene pentamine; secondary aliphatic amines such as dimethyl amine, diethyl amine, di-n-propyl amine, diisopropyl amine, di-n-butyl amine, diisobutyl amine, di-sec-butyl amine, dipentyl amine, dicyclopentyl amine, dihexyl amine, dicyclohexyl amine, diheptyl amine, dioctyl amine, dinonyl amine, didecyl amine, didodecyl amine, dicetyl amine, N,N-dimethyl methylene diamine, N,N-dimethyl ethylene diamine, and N,N-dimethyl tetraethylene pentamine; tertiary aliphatic amines such as trimethyl amine, triethyl amine, tri-n-propyl amine, triisopropyl amine, tri-n-butyl amine, triisobutyl amine, tri-sec-butyl amine, tripentyl amine, tricyclopentyl amine, trihexyl amine, tricyclohexyl amine, triheptyl amine, trioctyl amine, trinonyl amine, tridecyl amine, tridodecyl amine, tricetyl amine, N,N,N',N'-tetramethyl methylene diamine, N,N,N',N'-tetramethyl ethylene diamine, and N,N,N',N'-tetramethyl tetraethylene pentamine.

Examples of the mixed amines include dimethyl ethyl amine, methyl ethyl propyl amine, benzyl amine, phenetyl amine, and benzyl dimethyl amine. Specific examples of the aromatic amines and the heterocyclic amines include aniline derivatives (such as aniline, N-methyl aniline, N-ethyl aniline, N-propyl aniline, N,N-dimethyl aniline, 2-methyl aniline, 3-methyl aniline, 4-methyl aniline, ethyl aniline, propyl aniline, trimethyl aniline, 2-nitro aniline, 3-nitro aniline, 4-nitro aniline, 2,4-dinitro aniline, 2,6-dinitro aniline, 3,5-dinitro aniline, and N,N-dimethyl toluidine), diphenyl p-tolyl)amine, methyl diphenyl amine, triphenyl amine, phenylene diamine, naphthyl amine, diaminonaphthalene, pyrrole derivatives (such as pyrrole, 2H-pyrrole, 1-methyl pyrrole, 2,4-dimethyl pyrrole, 2,5-dimethyl pyrrole, and N-methyl pyrrole), oxazole derivatives (such as oxazole and isooxazole), thiazole derivatives (such as thiazole and isothiazole), imidazole derivatives (such as imidazole, 4-methyl imidazole, and 4-methyl-2-phenyl imidazole), a pyrazole derivative, a furazane derivative, pyrroline derivatives (such as pyrroline and 2-methyl-1-pyrroline), pyrrolidine derivatives (such as pyrrolidine, N-methyl pyrrolidine, pyrrolidinone, and N-methyl pyrrolidone), an imidazoline derivative, an imidazolidine derivative, pyridine derivatives (such as pyridine, methyl pyridine, ethyl pyridine, propyl pyridine, butyl pyridine, 4-(1-butylphenyl) pyridine, dimethyl pyridine, trimethyl pyridine, triethyl pyridine, phenyl pyridine, 3-methyl-2-phenyl pyridine, 4-tert-butyl pyridine, diphenyl pyridine, benzyl pyridine, methoxy pyridine, butoxy pyridine, dimethoxy pryridine, 4-pyrrolidino pyridine, 2-(1-ethylpropyl)pyridine, amino pyridine, and dimethylamino pyridine), a pyridazine derivative, a pyrimidine derivative, a pyrazine derivative, a pyrazoline derivative, a pyrazolidine derivative, a piperidine derivative, a piperazine derivative, a morpholine derivative, an indole derivative, an isoindole derivative, a 1H-indazole derivative, an indoline derivative, quinoline derivatives (such as quinoline and 3-quinoline carbonitrile), an isoquinoline derivative, a cinnoline derivative, a quinazoline derivative, a quinoxaline derivative, a phthalazine derivative, a purine derivative, a pteridine derivative, a carbazole derivative, a phenanthridine derivative, an acridine derivative, a phenazine derivative, a 1,10-phenanthroline derivative, an adenine derivative, an adenosine derivative, a guanine derivative, a guanosine derivative, an uracil derivative, and a uridine derivative.

Examples of the nitrogen-containing compound having a carboxy group include amino benzoic acid, indole carboxylic acid, and amino acid derivatives (such as nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxyalanine). Examples of the nitrogen-containing compound having a sulfonyl group include 3-pyridine sulfonic acid and pyridinium p-toluene sulfonate. Examples of the nitrogen-containing compound having a hydroxyl group, the nitrogen-containing compound having a hydroxyphenyl group, and the alcoholic nitrogen-containing compounds include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl) morpholine, 2-(2-hydroxyethyl) pyridine, 1-(2-hydroxyethyl)piperazine, 1-[2-(2-hyroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propane diol, 3-pyrrolidino-1,2-propane diol, 8-hydroxy julolidine, 3-quinuclidinol, 3-tropanol, 1-methyl-2-pyrrolidine ethanol, 1-azilidine ethanol, N-(2-hydroxyethyl) phthalimide, and N-(2-hydroxyethyl)isonicotinamide. Examples of the amides include formamide, N-methyl formamide, N,N-dimethyl formamide, acetamide, N-methyl acetamide, N,N-dimethyl acetamide, propionamide, benzamide, and 1-cyclohexyl pyrrolidone. Examples of the imides include phthalimide, succinimide, and maleimide. Examples of the carbamates include N-t-butoxycarbonyl-N,N-dicyclohexyl amine, N-t-butoxycarbonyl benzimidazole, and oxazolidinone.

In addition, there may be mentioned a nitrogen-containing organic base represented by the following general formula (a)-1:

$$N(X)_{n'}(Y)_{3-n'} \quad (a)\text{-}1$$

wherein, a reference character "n'" represents 1, 2, or 3; a side chain X may be the same or different, represented by the following general formulae (X1) to (X3); a side chain Y may be the same or different, representing a hydrogen atom, or a linear, a branched, or a cyclic alkyl group having 1 to 20 carbon atoms optionally containing an ether group or a hydroxyl group; and X may form a ring by bonding with each other.

$$-R^1-O-R^2 \quad (X1)$$

$$-R^3-O-R^4-CO-R^5 \quad (X2)$$

$$-R^6-COO-R^7 \quad (X3)$$

In the above formulae (X1) to (X3), $R^1$, $R^3$, and $R^6$ represent a linear or a branched alkylene group having 1 to 4 carbon atoms, and $R^2$ and $R^5$ represent a hydrogen atom, or a linear, a branched, or a cyclic alkyl group having 1 to 20 carbon atoms and optionally containing one or more groups selected from a hydroxyl group, an ether group, an ester group, and a lactone ring. $R^4$ represents a single bond, or a linear or a branched alkylene group having 1 to 4 carbon atoms, and $R^7$ represents a linear, a branched, or a cyclic alkyl group having 1 to 20 carbon atoms and optionally containing one or more groups selected from a hydroxyl group, an ether group, an ester group, and a lactone ring.

Specific examples of the compounds represented by the general formula (a)-1 include tris(2-methoxymethoxyethyl) amine, tris{2-(2-methoxyethoxy)ethyl} amine, tris{2-(2-methoxyethoxymethoxy)ethyl} amine, tris{2-(1-methoxyethoxy)ethyl} amine, tris{2-(1-ethoxyethoxy)ethyl} amine, tris{2-(1-ethoxypropoxy)ethyl} amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5,1-aza-18-crown-6, tris(2-formyloxyethyl)amine, tris(2-acetoxyethyl)amine, tris(2-propionyloxyethyl) amine, tris(2-butyryloxyethyl) amine, tris(2-isobutyryloxyethyl) amine, tris(2-valeryloxyethyl) amine, tris(2-pivaloyloxyethyl)amine, N,N-bis(2-acetoxyethyl) 2-(acetoxyacetoxy) ethyl amine, tris(2-methoxycarbonyloxyethyl) amine, tris(2-tert-butoxycarbonyloxyethyl) amine, tris[2-(2-oxopropoxy) ethyl]amine, tris[2-(methoxycarbonylmethyl)oxyethyl] amine, tris[2-(tert-butoxycarbonylmethyloxy)ethyl] amine, tris[2-(cyclohexyloxycarbonylmethyloxy)ethyl] amine, tris (2-methoxycarbonyl ethyl) amine, tris(2-ethoxycarbonylethyl) amine, N,N-bis(2-hydroxyethyl) 2-(methoxycarbonyl) ethyl amine, N,N-bis(2-acetoxyethyl) 2-(methoxycarbonyl) ethyl amine, N,N-bis(2-hydroxyethyl) 2-(ethoxycarbonyl) ethyl amine, N,N-bis(2-acetoxyethyl) 2-(ethoxycarbonyl) ethyl amine, N,N-bis(2-hydroxyethyl) 2-(2- methoxyethoxycarbonyl)ethyl amine, N,N-bis(2-acetoxyethyl) 2-(2-methoxyethoxycarbonyl)ethyl amine, N,N-bis(2-hydroxyethyl) 2-(2-hydroxyethoxycarbonyl)ethyl amine, N,N-bis(2-acetoxyethyl) 2-(2-acetoxyethoxycarbonyl)ethyl amine, N,N-bis(2-hydroxyethyl) 2-[(methoxycarbonyl)methoxycarbonyl]ethyl amine, N,N-bis(2-acetoxyethyl) 2-[(methoxycarbonyl)methoxycarbonyl]ethyl amine, N,N-bis(2-hydroxyethyl) 2-(2-oxopropoxycarbonyl)ethyl amine, N,N-bis(2-acetoxyethyl) 2-(2-oxopropoxycarbonyl)ethyl amine, N,N-bis(2-hydroxyethyl) 2-(tetrahydrofurfuryloxycarbonyl)ethyl amine, N,N-bis(2-acetoxyethyl) 2-(tetrahydrofurfuryloxycarbonyl)ethyl amine, N,N-bis(2-hydroxyethyl) 2-[(2-oxotetrahydrofurane-3-yl)oxycarbonyl]ethyl amine, N,N-bis(2-acetoxyethyl) 2-[(2-oxotetrahydrofurane-3-yl)oxycarbonyl]ethyl amine, N,N-bis(2-hydroxyethyl) 2-(4-hydroxybutoxycarbonyl)ethyl amine, N,N-bis(2-formyloxyethyl) 2-(4-formyloxybutoxycarbonyl)ethyl amine, N,N-bis(2-formyloxyethyl) 2-(2-formyloxyethoxycarbonyl)ethyl amine, N,N-bis(2-methoxyethyl) 2-(methoxycarbonyl)ethyl amine, N-(2-hydroxyethyl) bis[2-(methoxycarbonyl)ethyl] amine, N-(2-acetoxyethyl) bis[2-(methoxycarbonyl)ethyl] amine, N-(2-hydroxyethyl) bis[2-(ethoxycarbonyl)ethyl] amine, N-(2-acetoxyethyl) bis[2-(ethoxycarbonyl)ethyl] amine, N-(3-hydroxy-1-propyl) bis[2-(methoxycarbonyl)ethyl] amine, N-(3-acetoxy-1-propyl) bis[2-(methoxycarbonyl)ethyl] amine, N-(2-methoxyethyl) bis[2-(methoxycarbonyl)ethyl] amine, N-butyl bis[2-(methoxycarbonyl)ethyl] amine, N-butyl bis[2-(2-methoxyethoxycarbonyl)ethyl] amine, N-methyl bis(2-acetoxyethyl) amine, N-ethyl bis(2-acetoxyethyl) amine, N-methyl bis(2-pivaloyloxyethyl) amine, N-ethyl bis[2-(methoxycarbonyloxy)ethyl] amine, N-ethyl bis[2-(tert-butoxycarbonyloxy)ethyl] amine, tris(methoxycarbonylmethyl)amine, tris(ethoxycarbonylmethyl)amine, N-butyl bis(methoxycarbonylmethyl) amine, N-hexyl bis(methoxycarbonylmethyl)amine, and β-(diethylamino)-δ-valerolactone.

Further, there may be mentioned a nitrogen-containing organic base having a cyclic structure, as represented by the following general formula (a)-2:

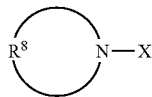

(a)-2 wherein, X represents the same as before, and $R^8$ represents a linear, or a branched alkylene group having 2 to 20 carbon atoms and optionally containing one or more groups selected from a carbonyl group, an ether group, an ester group, and a sulfide group.

Specific examples of the compound represented by the general formula (a)-2 include 1-[2-(methoxymethoxy)ethyl] pyrrolidine, 1-[2-(methoxymethoxy)ethyl] piperidine, 4-[2-(methoxymethoxy)ethyl] morpholin, 1-[2-[(2-methoxyethoxy)methoxy]ethyl] pyrrolidine, 1-[2-[(2-methoxyethoxy)methoxy]ethyl] piperidine, 4-[2-[(2-methoxyethoxy)methoxy]ethyl] morpholin, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl] morpholin, 1-[2-(t-butoxycarbonyloxy)ethyl] piperidine, 4-[2-(2-methoxyethoxycarbonyloxy)ethyl] morpholin, methyl 3-(1-pyrrolidinyl) propionate, methyl 3-piperidino propionate, methyl 3-morpholino propionate, methyl 3-(thiomorpholino) propionate, methyl 2-methyl-3-(1-pyrrolidinyl) propionate, ethyl 3-morpholino propionate, methoxycarbonylmethyl 3-piperidino propionate, 2-hydroxyethyl 3-(1-pyrrolidinyl) propionate, 2-acetoxyethyl 3-morpholino propionate, 2-oxotetrahydrofurane-3-yl 3-(1-pyrrolidinyl) propionate, tetrahydrofurfuryl 3-morpholino propionate, glycidyl 3-piperidino propionate, 2-methoxyethyl 3-morpholino propionate, 2-(2-methoxyethoxy)ethyl 3-(1-pyrrolidinyl) propionate, butyl 3-morpholino propionate, cyclohexyl 3-piperidino propionate, α-(1-pyrrolidinyl) methyl-γ-butyrolactone, β-piperidino-γ-butyrolactone, β-morpholino-δ-valerolactone, methyl 1-pyrrolidinyl acetate, methyl piperidino acetate, methyl morpholino acetate, methyl thiomorpholino acetate, ethyl 1-pyrrolidinyl acetate, 2-methoxyethyl morpholino acetate, 2-morpholinoethyl 2-methoxyacetate, 2-morpholinoethyl 2-(2-methoxyethoxy) acetate, 2-morpholinoethyl 2-[2-(2-methoxyethoxy)ethoxy] acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Further, there may be mentioned a nitrogen-containing organic base having a cyano group, as represented by the following general formulae (a)-3 to (a)-6:

(a)-3

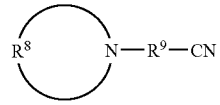

(a)-4

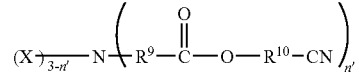

(a)-5

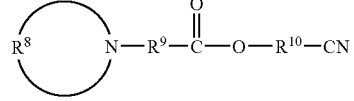

(a)-6 wherein X, $R^8$, and a reference character "n'" represent the same as before, and $R^9$ and $R^{10}$ represent the same or different linear or branched alkylene group having 1 to 4 carbon atoms.

Specific examples of the nitrogen-containing organic base having a cyano group represented by the above formulae (a)-3 to (a)-6 include 3-(diethylamino) propionitrile, N,N-bis(2-hydroxyethyl)-3-amino propionitrile, N,N-bis(2-acetoxyethyl)-3-amino propionitrile, N,N-bis(2-formyloxyethyl)-3-amino propionitrile, N,N-bis(2-methoxyethyl)-3-amino propionitrile, N,N-bis[2-(methoxymethoxy)ethyl]-3-amino propionitrile, methyl N-(2-cyanoethyl)-N-(2-methoxyethyl)-3-amino propionate, methyl N-(2-cyanoethyl)-N-(2-hydroxyethyl)-3-amino propionate, methyl N-(2-acetoxyethyl)-N-(2-cyanoethyl)-3-amino propionate, N-(2-cyanoethyl)-N-ethyl-3-amino propionitrile, N-(2-cyanoethyl)-N-(2-hydroxyethyl)-3-amino propionitrile, N-(2-acetoxyethyl)-N-(2-cyanoethyl)-3-amino propionitrile, N-(2-cyanoethyl)-N-(2-formyloxyethyl)-3-amino propionitrile, N-(2-cyanoethyl)-N-(2-methoxyethyl)-3-amino propionitrile, N-(2-cyanoethyl)-N-[2-(methoxymethoxy)ethyl]-3-amino propionitrile, N-(2-cyanoethyl)-N-(3-hydroxy-1-propyl)-3-amino propionitrile, N-(3-acetoxy-1-propyl)-N-(2-cyanoethyl)-3-amino propionitrile, N-(2-cyanoethyl)-N-(3-formyloxy-1-propyl)-3-amino propionitrile, N-(2- cyanoethyl)-N-tetrahydrofurfuryl-3-amino propionitrile, N,N-bis(2-cyanoethyl)-3-amino propionitrile, diethylamino acetonitrile, N,N-bis(2-hydroxyethyl)amino acetonitrile, N,N-bis(2-acetoxyethyl)amino acetonitrile, N,N-bis(2-formyloxyethyl)amino acetonitrile, N,N-bis(2-methoxyethyl)amino acetonitrile, N,N-bis[2-(methoxymethoxy)ethyl]amino acetonitrile, methyl N-cyanomethyl-N-(2-methoxyethyl)-3-amino propionate, methyl N-cyanomethyl-N-(2-hydroxyethyl)-3-amino propionate, methyl N-(2-acetoxyethyl)-N-cyanomethyl-3-amino propionate, N-cyanomethyl-N-(2-hydroxyethyl)amino acetonitrile, N-(2-acetoxyethyl)-N-(cyanomethyl)amino acetonitrile, N-cyanomethyl-N-(2-formyloxyethyl)amino acetonitrile, N-cyanomethyl-N-(2-methoxyethyl)amino acetonitrile, N-cyanomethyl-N-[2-(methoxymethoxy)ethyl]amino acetonitrile, N-(cyanomethyl)-N-(3-hydroxy-1-propyl)amino acetonitrile, N-(3-acetoxy-1-propyl)-N-(cyanomethyl) amino acetonitrile, N-cyanomethyl-N-(3-formyloxy-1-propyl)amino acetonitrile, N,N-bis(cyanomethyl)amino acetonitrile, 1-pyrrolidine propionitrile, 1-piperidine propionitrile, 4-morpholin propionitrile, 1-pyrolidine acetonitrile, 1-piperidine acetonitrile, 4-morpholin acetonitrile, cyanomethyl 3-diethylamino propionate, cyanomethyl N,N-bis(2-hydroxyethyl)-3-amino propionate, cyanomethyl N,N-bis(2-acetoxyethyl)-3-amino propionate, cyanomethyl N,N-bis(2-formyloxyethyl)-3-amino propionate, cyanomethyl N,N-bis(2-methoxyethyl)-3-amino propionate, cyanomethyl N,N-bis[2-(methoxymethoxy)ethyl]-3-amino propionate, (2-cyanoethyl) 3-diethylamino propionate, (2-cyanoethyl) N,N-bis(2-hydroxyethyl)-3-amino propionate, (2-cyanoethyl) N,N-bis(2-acetoxyethyl)-3-amino propionate, (2-cyanoethyl)N,N-bis(2-formyloxyethyl)-3-amino propionate, (2-cyanoethyl)N,N-bis(2-methoxyethyl)-3-amino propionate, (2-cyanoethyl)N,N-bis[2-(methoxymethoxy)ethyl]-3-amino propionate, cyanomethyl 1-pyrrolidine propionate, cyanomethyl 1-piperidine propionate, cyanomethyl 4-morpholin propionate, (2-cyanoethyl) 1-pyrolidine propionate, (2-cyanoethyl) 1-piperidine propionate, and (2-cyanoethyl) 4-morpholin propionate.

Further, there may be mentioned a nitrogen-containing organic base having an imidazole skeleton and a polar functional group, as represented by the following general formula (a)-7:

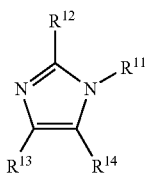

(a)-7 wherein, $R^{11}$ represents a linear, a branched, or a cyclic alkyl group having 2 to 20 carbon atoms and containing any one or more of polar functional groups selected from a hydroxyl group, a carbonyl group, an ester group, an ether group, a sulfide group, a carbonate group, a cyano group, and an acetal group; and $R^{12}$, $R^{13}$, and $R^{14}$ represent a hydrogen atom, a linear, a branched, or a cyclic alkyl, aryl, or aralkyl group having 1 to 10 carbon atoms.

Further, there may be mentioned a nitrogen-containing organic base having a benzimidazole skeleton and a polar functional group, as represented by the following general formula (a)-8:

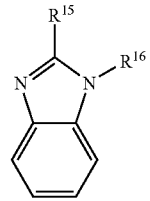

(a)-8 wherein, $R^{15}$ represents a hydrogen atom, or a linear, a branched, or a cyclic alkyl, aryl, or aralkyl group having 1 to 10 carbon atoms; $R^{16}$ represents a linear, a branched, or a cyclic alkyl group having 1 to 20 carbon atoms and containing any one or more of polar functional groups selected from an ester group, an acetal group, and a cyano group, and in addition, optionally containing any one or more of groups selected from a hydroxyl group, a carbonyl group, an ether group, a sulfide group, and a carbonate group.

Further, there may be mentioned a nitrogen-containing organic base having a polar functional group, as represented by the following general formulae (a)-9 and (a)-10:

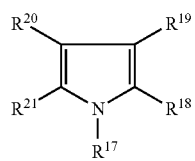

(a)-9

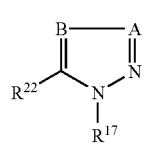

(a)-10 wherein, A represents a nitrogen atom or =C—$R^{23}$; B represents a nitrogen atom or =C—$R^{24}$; $R^{17}$ represents a linear, a branched, or a cyclic alkyl group having 2 to 20 carbon atoms and containing one or more polar functional groups selected from a hydroxyl group, a carbonyl group, an ester group, an ether group, a sulfide group, a carbonate group, a cyano group, and an acetal group; $R^{18}$, $R^{19}$, $R^{20}$, and $R^{21}$ represent a hydrogen atom, a linear, a branched, a cyclic alkyl or an aryl groups having 1 to 10 carbon atoms, or $R^{18}$ and $R^{19}$, and $R^{20}$ and $R^{21}$ may be bonded with each other to form a benzene ring, a naphthalene ring, or a pyridine ring; $R^{22}$ represents a hydrogen atom, a linear, a branched, a cyclic alkyl or an aryl group having 1 to 10 carbon atoms; $R^{23}$ and $R^{24}$ represent a hydrogen atom, a linear, a branched, a cyclic alkyl or an aryl group having 1 to 10 carbon atoms,; and $R^{22}$ and $R^{24}$ may be bonded to form a benzene ring or a naphthalene ring.

Further, there may be mentioned a nitrogen-containing organic base having an aromatic carboxylate ester structure, as represented by the following general formulae (a)-11 to (a)-14:

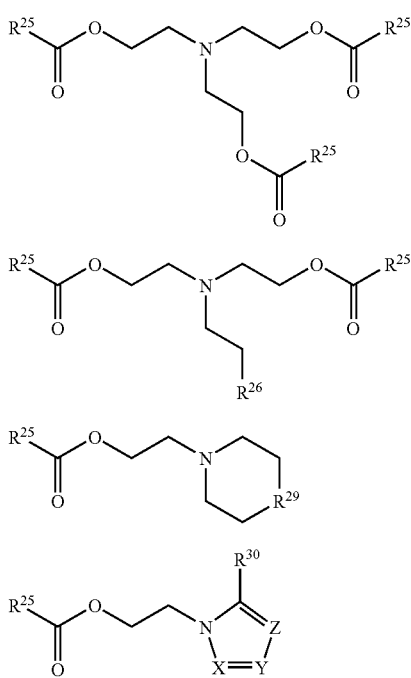

(a)-11

(a)-12

(a)-13

(a)-14 wherein, $R^{25}$ represents an aryl group having 6 to 20 carbon atoms and a hetero aromatic group having 4 to 20 carbon atoms, and a part or all of their hydrogen atoms may be substituted by a halogen atom, a linear, a branched, or a cyclic alkyl group having 1 to 20 carbon atoms, an aryl group having 6 to 20 carbon atoms, an aralkyl group having 7 to 20 carbon atoms, an alkoxy group having 1 to 10 carbon atoms, an acyloxy group having 1 to 10 carbon atoms, or an alkylthio group having 1 to 10 carbon atoms; $R^{26}$ represents $CO_2R^{27}$, $OR^{28}$, or a cyano group; $R^{27}$ represents an alkyl group having 1 to 10 carbon atoms whose methylene group may be partly substituted by an oxygen atom; $R^{28}$ represents an alkyl or an acyl group having 1 to 10 carbon atoms whose methylene group may be partly substituted by an oxygen atom; $R^{29}$ represents a single bond, a methylene group, an ethylene group, a sulfur atom, or a $-O(CH_2CH_2O)_n-$ group; a reference character "n" represents 0, 1, 2, 3, or 4; $R^{30}$ represents a hydrogen atom, a methyl group, an ethyl group, or a phenyl group; X represents a nitrogen atom or a $CR^{31}$ group; Y represents a nitrogen atom or a $CR^{32}$ group; Z represents a nitrogen atom or a $CR^{33}$ group; and each of $R^{31}$, $R^{32}$, and $R^{33}$ independently represents a hydrogen atom, a methyl group, or a phenyl group, or $R^{31}$ and $R^{32}$, or $R^{32}$ and $R^{33}$ may be bonded to form an aromatic ring having 6 to 20 carbon atoms or a hetero aromatic ring having 2 to 20 carbon atoms.

Further, there may be mentioned a nitrogen-containing organic base having a 7-oxanorbornane-2-carboxylate ester structure, as represented by the following general formula (a)-15:

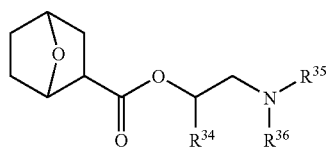

(a)-15 wherein, $R^{34}$ represents a hydrogen atom, or a linear, a branched, or a cyclic alkyl group having 1-10 carbon atoms; $R^{35}$ and $R^{36}$ independently represent an alkyl group having 1 to 20 carbon atoms, an aryl group having 6 to 20 carbon atoms, or an aralkyl group having 7 to 20 carbon atoms and optionally containing one or more polar functional groups including an ether, a carbonyl, an ester, an alcohol, a thio group, a nitrile, an amine, an imine, and an amide, wherein a part of hydrogen atoms therein may be optionally substituted by a halogen atom; and $R^{35}$ and $R^{36}$ may be bonded with each other to form a heterocyclic ring or a heteroaromatic ring having 2 to 20 carbon atoms.

The nitrogen-containing organic base used as the catalyst contained in a mixture along with a silane compound is preferably, among the nitrogen-containing organic bases as mentioned above, a nitrogen-containing organic base containing a structure as represented by the following general formula (a)-16:

(a)-16 wherein, $R^{37}$ represents a linear or a branched alkylene group having 2 to 20 carbon atoms and optionally containing one or more groups selected from a carbonyl group, an ether group, an ester group, and a sulfide group; $R^{38}$ represents a hydrogen atom, or a linear or a branched alkylene group optionally containing one or more groups selected from a hydroxyl group, a carbonyl group, an ether group, an ester group, and a lactone ring.

It is known that condensation of a silane compound can be further accelerated especially in an aqueous basic solution. However, an action of a base in an organic solvent is not known well. From the study in the present invention, it became clear that a monomolecular film may be more easily formed when a nitrogen-containing organic base formed of the above-mentioned cyclic structure is used.

By a further study, it became clear that a monomolecular film may be even more easily formed when a pyrrolidine derivative or a piperidine derivative is used as the nitrogen-containing organic base.

Namely, the nitrogen-containing organic base is exemplified more preferably by a pyrrolidine derivative and a piperidine derivative, and further more preferably by pyrrolidine, N-methyl pyrrolidine, piperidine, and N-methyl piperidine. However, the nitrogen-containing organic base is not limited to them.

Examples of the solvent used to form a monomolecular film having orientated oxysilanyl groups toward an outmost surface include ketones such as cyclohexanone and methyl-2-n-amyl ketone; alcohols such as 3-methoxy butanol, 3-methyl-3-methoxy butanol, 1-methoxy-2-propanol, and 1-ethoxy-2-propanol; ethers such as propyleneglycol monomethyl ether, ethyleneglycol monomethyl ether, propyleneglycol monoethyl ether, ethyleneglycol monoethyl ether, propyleneglycol dimethyl ether, and diethyeneglycol dimethyl ether; esters such as propyleneglycol monomethyl ether acetate, propyleneglycol monoethyl ether acetate, ethyl lactate, ethyl pilvate, butyl acetate, methyl 3-methoxypropionate, ethyl 3-ethoxy propionate, tert-butyl acetate, tert-butyl propionate, and propylene glycol mono-tert-butyl ether acetate; lactones such as γ-butyrolactone; hydrocarbons such as n-hexane and n-nonane; aromatic hydrocarbons such as benzene and toluene; and chloroform and the like. They may be used singly or in a combination of two or more kinds, though not limited to these solvents.

In order to form a monomolecular film having orientated oxysilanyl groups toward an outmost surface by the above-mentioned silane compound having an oxysilanyl group, a laminated substrate whose unintended part may be protected by a resist is soaked in a solvent with an extremely low polarity containing a silane compound represented by the general formula (2) or its mixture with a silane compound represented by the general formula (3) or (4) with their concentration being relatively low, for example, $2.0 \times 10^{-2}$ to $5.0 \times 10^{-2}$ mol/L, and further containing a nitrogen-containing organic base with its concentration being, for example, $2.0 \times 10^{-2}$ to $5.0 \times 10^{-2}$ mol/L, and with a time being, for example, 24 hours in the case of a triethoxy silane compound.

In the present invention, it is preferable that a concentration ratio of the silane compound and the nitrogen-containing organic base be made such that a mol ratio of the nitrogen-containing organic base is 0.1 to 100 by mol relative to 1 mol of the silane compound in order to easily form a monomolecular film.

After the treatment as mentioned above, when a monomolecular film is formed regioselectively by using a resist film, a substrate having orientated oxysilanyl groups toward an outmost surface may be obtained by removing the resist pattern by an organic solvent dissolvable the resist film, such as propyleneglycol monomethyl ether and ethyl lactate, a solvent generally used for preparing a resist solution.

After the treatment as mentioned above, a substrate having amino groups orientated toward an outmost surface may be obtained by soaking the substrate having orientated oxysilanyl groups toward an outmost surface in a solution containing a diamine compound. A diamine compound of the present invention is preferably the one represented by the following general formula (1):

$$NH_2\text{-}Z\text{-}NH_2 \quad (1)$$

wherein Z represents a linear, a branched, or a cyclic divalent alkylene group having 1 to 20 carbon atoms with a hydrogen atom contained in the group being optionally substituted by a halogen atom, a hydroxyl group, and a cyano group, and a methylene group in the group being optionally substituted by an oxygen atom (—O—) or a carbonyloxy group (—O—CO—) and optionally containing a double bond (C═C) or a triple bond (C≡C).

When using a method of the present invention, the diamine compound is more preferably the one containing a carbon chain having 8 to 16 carbon atoms in the case of the structure between two amino groups being linear or branched (and optionally containing one or more double bonds in the carbon chain) and the one containing an aryl group in the case of the structure being cyclic. With this, a monomolecular film can be made by an intermolecular interaction, namely by a self-assembly, so that the amino groups having high resistances to delamination and to the subsequent processing operations of the substrate may be orientated stably toward an outmost surface on a substrate. These compounds may be substituted by a methyl group, an ethyl group, a halogen atom, a hydroxyl group, and a nitrile group on their side chain.

In addition, the solution containing a diamine compound may contain an amine compound having the same Z as the diamine compound in the general formula (1) with one of the two amino groups bonded to Z being a methyl group. With this, a surface wetting property may be manipulated, leading to a significant meaning in the production in a certain case.

Specific examples of the diamine compound in the present invention include the following compounds.

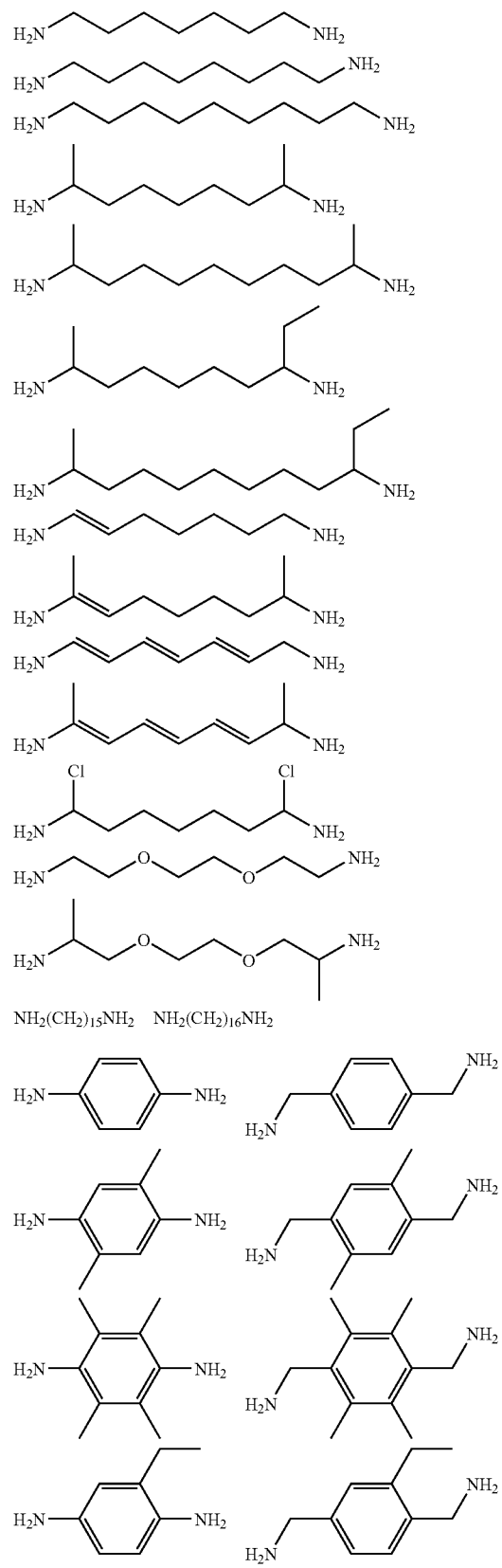

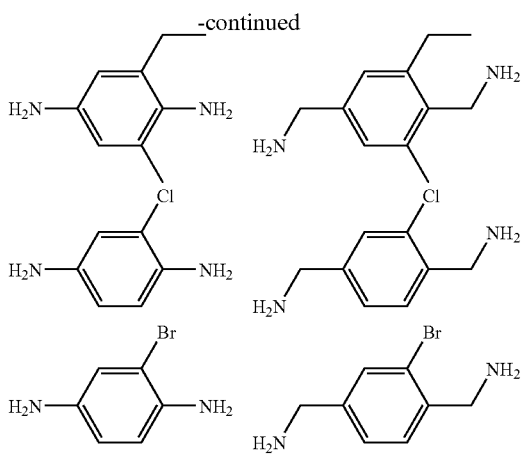

Examples of the solvents used for forming a monomolecular film having orientated amino groups toward an outmost surface in the present invention include water; ketones such as cyclohexanone and methyl-2-amyl ketone; alcohols such as methanol, ethanol, 3-methoxy butanol, 3-methyl-3-methoxy butanol, and 1-methoxy-2-propanol; ethers such as propyleneglycol monomethyl ether, ethyleneglycol monomethyl ether, propyleneglycol monoethyl ether, ethyleneglycol monoethyl ether, propyleneglycol dimethyl ether, and diethyleneglycol dimethyl ether; esters such as propyleneglycol monomethyl ether acetate, propyleneglycol monoethyl ether acetate, ethyl lactate, ethyl pilvate, butyl acetate, methyl 3-methoxypropionate, ethyl 3-ethoxy propionate, tert-butyl acetate, tert-butyl propionate, and propylene glycol mono-tert-butyl ether acetate; lactones such as γ-butyrolactone; hydrocarbons such as n-hexane and n-nonane; aromatic hydrocarbons such as benzene and toluene; and chloroform and the like. They may be used singly or in a combination of two or more kinds, though not limited to these solvents.

Concentration of a diamine at the time of formation of the above-mentioned monomolecular film having orientated amine groups is preferably 0.02 mol/L or less. This is desirable from a view point to avoid an etching of the substrate itself by an action of oxide etching due to a hydroxide ion formed by action of a diamine with a solvent water or with water contained in a solvent.

After the treatment as mentioned above, a substrate for making a microarray containing a monomolecular film having orientated amino groups toward an outmost surface is completed.

EXAMPLES

Hereinafter, the present invention will be described specifically by Examples and Comparative Example, but is not restricted by the following Examples and the like. Here, FIG. 1 illustrates a method for producing a substrate for making a microarray of the present invention used in the Examples to be described hereinafter.

Production Example 1

Production of 11,12-Epoxydodecyl Trimethoxy Silane

The compound was produced according to the method described in Japanese Patent Application Laid-Open (kokai) No. H4-182491.

Measurement results of IR (liquid film), $^{13}$C-NMR, and $^{1}$H-NMR of 11,12-epoxydodecyl trimethoxy silane thereby produced are shown below.

IR (liquid film) $v_{max}$: 3041, 2925, 2854, 2840, 1727, 1465, 1911, 1089, and 916 cm$^{-1}$.

$^{13}$C-NMR (150 MHz, CDCl$_3$) δ: 9.10, 22.54, 25.92, 29.18, 29.39, 29.40, 29.42, 29.48, 32.45, 33.08, 47.07, 50.42, and 52.35 ppm.

$^{1}$H-NMR (600 MHz, CDCl$_3$) δ: 0.59 to 0.62 (2H, m), 1.20 to 1.51 (20H, m), 2.421 (1H, dd, J=3.5 Hz), 2.70 (1H, t-like, J=5 Hz), and 2.85 to 2.88 (1H, m) ppm.

Example 1

A substrate 1a having a silicon oxide layer on its surface was washed under an ultrasonic wave by soaking in chloroform and then in acetone. The substrate was further soaked in a piranha solution for 15 minutes, in water for one hour, and then in a toluene solution containing 0.02 mol/L of 11,12-epoxydodecyl trimethoxy silane prepared as mentioned above and 0.02 mol/L of piperidine for 12 hours to form a monomolecular film 2b having orientated oxysilanyl groups toward an outmost surface on the substrate (FIG. 1(1)). The substrate was washed under an ultrasonic wave by soaking in chloroform, acetone, and then water for 5 minutes each.

The substrate 1a thus treated was soaked in a methanol solution containing 0.01 mol/L of 1,8-diamino octane for 8 hours to form a monomolecular film 3c having orientated amino groups toward an outmost surface on the substrate (FIG. 1(2)). The substrate was washed under an ultrasonic wave by soaking in chloroform, acetone, and then water for 5 minutes each.

The substrate 1a thus treated was further soaked in an aqueous solution containing 0.025 mol/L of maleic anhydride for 20 minutes to form a malice acid layer 4d (FIG. 1(3)). The substrate was washed by water and then by methanol, and thereafter dried by a dry air.

Example 2

A substrate having a silicon oxide layer on its surface was washed under an ultrasonic wave by soaking in chloroform and then in acetone. The substrate was further soaked in a piranha solution for 15 minutes, in water for one hour, and then in a toluene solution containing 0.02 mol/L of the above-mentioned 11,12-epoxydodecyl trimethoxy silane and 0.02 mol/L of piperidine for 12 hours to form a monomolecular film having orientated oxysilanyl groups toward an outmost surface on the substrate. The substrate was washed under an ultrasonic wave by soaking in chloroform, acetone, and then water for 5 minutes each.

The substrate thus treated was soaked in a methanol solution containing 0.01 mol/L of 2,5-diamino toluene for 8 hours to form a monomolecular film having orientated amino groups toward an outmost surface on the substrate. The substrate was washed under an ultrasonic wave by soaking in chloroform, acetone, and then water for 5 minutes each.

The substrate thus treated was further soaked in an aqueous solution containing 0.025 mol/L of maleic anhydride for 20 minutes, washed by water and then by methanol, and thereafter dried by a dry air.

Example 3

A substrate having a silicon oxide layer on its surface was washed under an ultrasonic wave by soaking in chloroform and then in acetone. The substrate was further soaked in a piranha solution for 15 minutes, in water for one hour, and then in a toluene solution containing 0.02 mol/L of the above-mentioned 11,12-epoxydodecyl trimethoxy silane, 0.02 mol/L of decyl trimethoxy silane, and 0.02 mol/L of piperidine for 12 hours to form a monomolecular film having orientated oxysilanyl groups toward an outmost surface on the substrate. The substrate was washed under an ultrasonic wave by soaking in chloroform, acetone, and then water for 5 minutes each.

The substrate thus treated was soaked in a methanol solution containing 0.01 mol/L of 2,5-diamino phenol for 8 hours to form a monomolecular film having orientated amino groups toward an outmost surface on the substrate. The substrate was washed under an ultrasonic wave by soaking in chloroform, acetone, and then water for 5 minutes each.

The substrate thus treated was further soaked in an aqueous solution containing 0.025 mol/L of maleic anhydride for 20 minutes, washed by water and then by methanol, and thereafter dried by a dry air.

Example 4

A substrate having a silicon oxide layer on its surface was washed under an ultrasonic wave by soaking in chloroform and then in acetone. The substrate was further soaked in a piranha solution for 15 minutes, in water for one hour, and then in a toluene solution containing 0.02 mol/L of the above-mentioned 11,12-epoxydodecyl trimethoxy silane and 0.02 mol/L of piperidine for 12 hours to form a monomolecular film having orientated oxysilanyl groups toward an outmost surface on the substrate. The substrate was washed under an ultrasonic wave by soaking in chloroform, acetone, and then water for 5 minutes each.

The substrate thus treated was soaked in a methanol solution containing 0.01 mol/L of ethylenediamine for 8 hours to form a monomolecular film having orientated amino groups toward an outmost surface on the substrate. The substrate was washed under an ultrasonic wave by soaking in chloroform, acetone, and then water for 5 minutes each.

The substrate thus treated was further soaked in an aqueous solution containing 0.025 mol/L of maleic anhydride for 20 minutes, washed by water and then by methanol, and thereafter dried by a dry air.

Comparative Example

A substrate having a silicon oxide layer on its surface was washed under an ultrasonic wave by soaking in chloroform and then in acetone. The substrate was further soaked in a piranha solution for 15 minutes, in water for one hour, and then in an acetone solution containing 5% by weight of 3-aminopropyl triethoxy silane and 2% by weight of triethyl amine. Thereafter, the substrate was washed by acetone for several times and then dried at 110° C. for 20 minute.

The substrate thus treated was further soaked in an aqueous solution containing 0.025 mol/L of maleic anhydride for 20 minutes, washed by water and then by methanol, and thereafter dried by a dry air.
(Thymidine Attachment)

In a nitrogen-replaced glove box, 5'-O-(4,4'-dimethoxytrityl)thymidine and N,N'-diisoproyl carbodiimide were dissolved in dehydrated pyridine with a concentration of 0.1 mol/L and 0.2 mol/L, respectively.

Then, each substrate obtained in Examples 1 to 4 and Comparative Example was soaked in the thus obtained solution for 1 minute. In this way, thymidine 5e whose terminal was substituted by a dimethoxy trityl group was attached to the substrate (FIG. 1(4)). Then the substrate was washed by THF and acetone, soaked in an aqueous iodine solution (0.1 mol/L), and washed by water and methanol.

Each of the obtained substrates was soaked in a dichloromethane solution containing 3% trichlroroacetaic acid, and then an UV-visible absorption spectrum of the resulting dichloromethane solution was measured. A red absorption peak at 504 nm is due to a dimethoxytrityl cation chromophore liberated by the acid so that the absorption may be observed if thymidine is immobilized on the substrate. It can also be seen that density of the immobilized thymidine is higher with a higher absorption.

Similar operation for thymidine attachment was repeated for three times in total by using the same substrate, and the absorption of each dichloromethane solution was measured. The results are shown in Table 1.

TABLE 1

|  | Absorbance (first) | Absorbance (second) | Absorbance (third) |
| --- | --- | --- | --- |
| Example 1 | 0.10 | 0.09 | 0.08 |
| Example 2 | 0.10 | 0.09 | 0.08 |
| Example 3 | 0.10 | 0.09 | 0.08 |
| Example 4 | 0.03 | 0.025 | 0.022 |
| Comparative Example | 0.015 | 0.005 | 0 |

From the results in Table 1, although a decrease in the absorption accompanying the yield of the attachment can be seen in Example 1 to 3, good results with no difference are obtained. In Example 4, although the absorption is low, a decrease in the absorbance accompanying the repetition is almost proportional to a decrease in the yield of the attachment. On the other hand, in Comparative Example, not only the absorbance is low, but also a decrease in absorbance by repetition is eminent.

Film thickness on each of the substrates is measured by an ellipsometry, and the results are shown in Table 2.

TABLE 2

|  | Film thickness (first) | Film thickness (second) | Film thickness (third) |
| --- | --- | --- | --- |
| Example 1 | 6.0 nm | 6.8 nm | 7.4 nm |
| Example 2 | 6.0 nm | 6.8 nm | 7.4 nm |
| Example 3 | 6.0 nm | 6.8 nm | 7.4 nm |
| Example 4 | 3.0 nm | 3.2 nm | 3.2 nm |
| Comparative Example | 0.5 nm | 0.1 nm | 0.0 nm |

From the results in Table 2, an increase in film thickness accompanying lamination of thymidine can be seen in Example 1 to 3. In Example 4, there is no decrease in film thickness, but the increase in film thickness accompanying lamination of thymidine is small, coinciding with the results of the UV-visible absorption spectra measurements. In Comparative Example, the film thickness is decreased accompanying the repetition, showing that the film itself is delaminated with the repetition. In conclusion, the results show that, in the substrate produced by a method of the present invention, delamination is small, and attachment of thymidine, one kind of biomolecules, is excellent.

It must be stated here that the present invention is not restricted to the embodiments as described above. The embodiments described above are merely exemplary so that any embodiment composed of substantially the same technical concept as described in claims of the present invention and expressing similar effects shown therein is included in the technical scope or the present invention.

What is claimed is:

1. A method for producing a substrate for making a microarray, the method comprising:
   a step of forming a monomolecular film having orientated oxysilanyl groups toward an outmost surface on a substrate; and
   a step of forming a monomolecular film having orientated amino groups toward an outmost surface on the substrate by applying to the oxysilanyl groups a solution containing a diamine compound represented by formula (1):

$$NH_2—Z—NH_2 \quad (1)$$

where:
   Z represents a cyclic divalent arylene group-containing group having 6 to 20 carbon atoms with a hydrogen atom in the group being optionally substituted by a halogen atom, a hydroxyl group, or a cyano group, and a methylene group in the group being optionally substituted by an oxygen atom (—O—) or a carbonyloxy group (—O—CO—);
   wherein:
   the step of forming the monomolecular film having orientated oxysilanyl groups toward an outmost surface on the substrate is performed by soaking the substrate in a solution containing a silane compound having an oxysilanyl group, the silane compound being represented by formula (2):

$$Y_3Si—(CH_2)_m—X \quad (2)$$

wherein:
   m represents an integer of 3 to 16;
   X represents an oxysilanyl group; and
   Y independently represents a halogen atom or an alkoxy group having 1 to 4 carbon atoms; and
   a catalyst that is a nitrogen-containing organic base is mixed into the solution containing the silane compound, the catalyst being selected from the group consisting of:
   a. a nitrogen-containing organic base represented by the following general formula (a)-1:

$$N(X)_{n'}(Y)_{3-n'} \quad (a)-1$$

wherein:
   n' represents 1, 2, or 3;
   a side chain X may be the same or different, represented by the following general formulae (X1) to (X3);
   a side chain Y may be the same or different, representing a hydrogen atom, or a linear, a branched, or a cyclic alkyl group having 1 to 20 carbon atoms optionally containing an ether group or a hydroxyl group; and
   X may form a ring by bonding with each other;

$$—R^1—O—R^2 \quad (X1)$$
   $$—R^3—O—R^4—CO—R^5 \quad (X2)$$
   $$—R^6—COO—R^7 \quad (X3)$$

wherein:
   $R^1$, $R^3$, and $R^6$ represent a linear or a branched alkylene group having 1 to 4 carbon atoms;
   $R^2$ and $R^5$ represent a hydrogen atom, or a linear, a branched, or a cyclic alkyl group having 1 to 20 carbon atoms and optionally containing one or more groups selected from a hydroxyl group, an ether group, an ester group, and a lactone ring;
   $R^4$ represents a single bond, or a linear or a branched alkylene group having 1 to 4 carbon atoms; and
   $R^7$ represents a linear, a branched, or a cyclic alkyl group having 1 to 20 carbon atoms and optionally containing one or more groups selected from a hydroxyl group, an ether group, an ester group, and a lactone ring;

b. a nitrogen-containing organic base having a cyano group represented by the following general formulae (a)-3 to (a)-6:

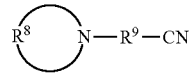

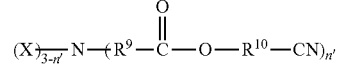

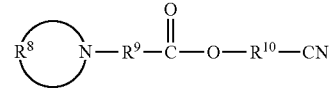

wherein:
   X and n' are as previously defined;
   $R^8$ represents a linear or a branched alkylene group having 2 to 20 carbon atoms and optionally containing one or more groups selected from a carbonyl group, an ether group, an ester group, and a sulfide group; and
   $R^9$ and $R^{10}$ represent the same or different linear or branched alkylene group having 1 to 4 carbon atoms;

c. a nitrogen-containing organic base having an imidazole skeleton and a polar functional group, as represented by the following general formula (a)-7:

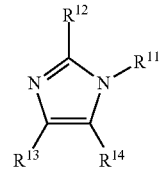

wherein:
   $R^{11}$ represents a linear, a branched, or a cyclic alkyl group having 2 to 20 carbon atoms and containing any one or more of polar functional groups selected from a hydroxyl group, a carbonyl group, an ester group, an ether group, a sulfide group, a carbonate group, a cyano group, and an acetal group; and
   $R^{12}$, $R^{13}$, and $R^{14}$ represent a hydrogen atom, a linear, a branched, or a cyclic alkyl, aryl, or aralkyl group having 1 to 10 carbon atoms;

d. a nitrogen-containing organic base having a benzimidazole skeleton and a polar functional group, as represented by the following general formula (a)-8:

(a)-8 wherein:
R$^{15}$ represents a hydrogen atom, or a linear, a branched, or a cyclic alkyl, aryl, or aralkyl group having 1 to 10 carbon atoms;
R$^{16}$ represents a linear, a branched, or a cyclic alkyl group having 1 to 20 carbon atoms and containing any one or more of polar functional groups selected from an ester group, an acetal group, and a cyano group, and in addition, optionally containing any one or more of groups selected from a hydroxyl group, a carbonyl group, an ether group, a sulfide group, and a carbonate group;

e. a nitrogen-containing organic base having a polar functional group, as represented by the following general formulae (a)-9 and (a)-10:

(a)-9

(a)-10 wherein:
A represents a nitrogen atom or =C—R$^{23}$;
B represents a nitrogen atom or =C—R$^{24}$;
R$^{17}$ represents a linear, a branched, or a cyclic alkyl group having 2 to 20 carbon atoms and containing one or more polar functional groups selected from a hydroxyl group, a carbonyl group, an ester group, an ether group, a sulfide group, a carbonate group, a cyano group, and an acetal group;
R$^{18}$, R$^{19}$, R$^{20}$, and R$^{21}$ represent a hydrogen atom, a linear, a branched, a cyclic alkyl or an aryl groups having 1 to 10 carbon atoms, or R$^{18}$ and R$^{19}$, and R$^{20}$ and R$^{21}$ may be bonded with each other to form a benzene ring, a naphthalene ring, or a pyridine ring;
R$^{22}$ represents a hydrogen atom, a linear, a branched, a cyclic alkyl or an aryl group having 1 to 10 carbon atoms;
R$^{23}$ and R$^{24}$ represent a hydrogen atom, a linear, a branched, a cyclic alkyl or an aryl group having 1 to 10 carbon atoms; and
R$^{22}$ and R$^{24}$ may be bonded to form a benzene ring or a naphthalene ring;

f. a nitrogen-containing organic base having an aromatic carboxylate ester structure, as represented by the following general formulae (a)-11 to (a)-14:

(a)-11

(a)-12

(a)-13

(a)-14 wherein:
R$^{25}$ represents an aryl group having 6 to 20 carbon atoms and a hetero aromatic group having 4 to 20 carbon atoms, and a part or all of their hydrogen atoms may be substituted by a halogen atom, a linear, a branched, or a cyclic alkyl group having 1 to 20 carbon atoms, an aryl group having 6 to 20 carbon atoms, an aralkyl group having 7 to 20 carbon atoms, an alkoxy group having 1 to 10 carbon atoms, an acyloxy group having 1 to 10 carbon atoms, or an alkylthio group having 1 to 10 carbon atoms;
R$^{26}$ represents CO$_2$R$^{27}$, OR$^{28}$, or a cyano group;
R$^{27}$ represents an alkyl group having 1 to 10 carbon atoms whose methylene group may be partly substituted by an oxygen atom;
R$^{28}$ represents an alkyl or an acyl group having 1 to 10 carbon atoms whose methylene group may be partly substituted by an oxygen atom;
R$^{29}$ represents a single bond, a methylene group, an ethylene group, a sulfur atom, or a —O(CH$_2$CH$_2$O)$_n$-group;
n represents 0, 1, 2, 3, or 4;
R$^3$ represents a hydrogen atom, a methyl group, an ethyl group, or a phenyl group;
X represents a nitrogen atom or a CR$^{31}$ group;
Y represents a nitrogen atom or a CR$^{32}$ group;
Z represents a nitrogen atom or a CR$^{33}$ group; and
each of R$^{31}$, R$^{32}$, and R$^{33}$ independently represents a hydrogen atom, a methyl group, or a phenyl group, or R$^{31}$ and R$^{32}$, or R$^{32}$ and R$^{33}$ may be bonded to form an aromatic ring having 6 to 20 carbon atoms or a hetero aromatic ring having 2 to 20 carbon atoms; and g. a nitrogen-containing organic base having a 7-oxanorbornane-2-carboxylate ester structure, as represented by the following general formula (a)-15:

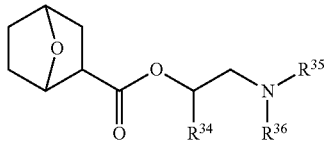

(a)-15 wherein:
- $R^{34}$ represents a hydrogen atom, or a linear, a branched, or a cyclic alkyl group having 1-10 carbon atoms;
- $R^{35}$ and $R^{36}$ independently represent an alkyl group having 1 to 20 carbon atoms, an aryl group having 6 to 20 carbon atoms, or an aralkyl group having 7 to 20 carbon atoms and optionally containing one or more polar functional groups including an ether, a carbonyl, an ester, an alcohol, a thio group, a nitrile, an amine, an imine, and an amide, wherein a part of hydrogen atoms therein may be optionally substituted by a halogen atom; and
- $R^{35}$ and $R^{36}$ may be bonded with each other to form a heterocyclic ring or a heteroaromatic ring having 2 to 20 carbon atoms.

2. The method according to claim 1, wherein, in the step of forming the monomolecular film having the orientated oxysilanyl groups toward an outmost surface on the substrate by using the silane compound having the oxysilanyl group represented by formula (2), the monomolecular film is formed by using a mixture prepared by mixing the silane compound with at least one silane compound represented by formulae (3) and (4):

$$Y'_3Si-(CH_2)_n-CH_3 \quad (3)$$

$$Y'_3Si-(CH_2)_n-OCH_3 \quad (4)$$

wherein:
- n represents an integer of 0 to m;
- m represents the value in formula (2); and
- Y' represents a halogen atom or an alkoxy group having 1 to 4 carbon atoms.

3. The method according to claim 1, wherein a concentration ratio of the silane compound and the nitrogen-containing organic base is made such that a mol ratio of the nitrogen-containing organic base is 0.1 to 100 by mol relative to 1 mol of the silane compound.

4. The method according to claim 1, wherein the microarray is used for testing of a biomolecule.

5. The method according to claim 4, wherein the biomolecule is a nucleic acid or a protein.

\* \* \* \* \*